United States Patent [19]

Tasset

[11] Patent Number: 4,602,110

[45] Date of Patent: Jul. 22, 1986

[54] METHOD OF PURIFYING 3-CHLORO-2-HYDROXYPROPYL TRIALKYLAMMONIUM CHLORIDE

[75] Inventor: Emmett L. Tasset, Lake Jackson, Tex.

[73] Assignee: The Dow Chemical Company, Midland, Mich.

[21] Appl. No.: 734,311

[22] Filed: May 15, 1985

[51] Int. Cl.$^4$ .............................................. C07C 89/04
[52] U.S. Cl. .................................................. 564/292
[58] Field of Search ........................ 564/292, 293, 294

[56] References Cited

U.S. PATENT DOCUMENTS

| | | | |
|---|---|---|---|
| 2,457,226 | 12/1948 | Gresham | 260/567.6 |
| 2,623,901 | 12/1952 | Klein | 260/567.6 |
| 2,744,934 | 5/1956 | Klein et al. | 564/293 |
| 2,803,651 | 8/1957 | Whiston et al. | 564/293 |
| 2,870,198 | 1/1959 | Klein et al. | 564/293 |
| 3,532,751 | 10/1970 | Langher et al. | 564/292 |
| 4,450,295 | 5/1984 | van der Mass | 564/292 |
| 4,480,126 | 10/1984 | Rutzen | 564/292 |

Primary Examiner—James H. Reamer
Attorney, Agent, or Firm—A. C. Ancona

[57] ABSTRACT

A method of purifying 3-chloro-2-hydroxypropyl trialkylammonium chloride. An aqueous slurry is prepared containing about 70–98 wt. % total solids including the chloride and impurities associated with the preparation thereof. To this slurry is then added a miscible alcohol having about 3–4 carbon atoms. A solid filtrate is collected and optionally washed with additional alcohol and dried. The solid filtrate is substantially more pure in the chloride than the starting material.

18 Claims, No Drawings

METHOD OF PURIFYING 3-CHLORO-2-HYDROXYPROPYL TRIALKYLAMMONIUM CHLORIDE

FIELD OF THE INVENTION

This invention relates to a method of purifying 3-chloro-2-hydroxypropyl trialkylammonium chloride which contains impurities typically formed during the reaction of epichlorohydrin with trialkylammonium hydrochloride.

BACKGROUND OF THE INVENTION

The reaction of epichlorohydrin with trimethylammonium hydrochloride in an aqueous medium to form 3-chloro-2-hydroxypropyl trimethylammonium chloride is well known. The resulting processed aqueous solution is commonly used to manufacture cationically active starch products. However, such an aqueous solution contains substantial quantities of by-products which are non-reactive in the starch manufacturing process, including, for example, 1,3-bis(trimethylammonium chloride)-2-hydroxypropane, and 1,2-hydroxypropane-3-trimethylammonium chloride.

These non-reactive impurities are not easily removed and can pose serious disposal problems to the cationically active starch manufacturers. These impurities can also cause a higher level of FDA extractable quaternarys in paper manufactured with non-washed cationic starch.

Another advantage to removing these impurities is the desire to transport more active 3-chloro-2-hydroxypropyl trialkylammonium chloride per pound of aqueous solution. Since the amount of total solids in the aqueous solution controls its freezing and crystallization point, the removal of these impurities allows a higher concentration of 3-chloro-2-hydroxypropyl trialkylammonium chloride per pound while effectively avoiding the freezing and crystallization point.

As far as Applicant is aware, there has been no method heretofore devised for removing these non-reactive impurities. The only method of which Applicant is aware which can be employed to obtain 3-chloro-2-hydroxypropyl trimethylammonium chloride free of substantial non-reactive impurities is described in U.S. Pat. No. 4,450,295. According to the method described in that patent, an aqueous trialkylammonium chloride solution was first prepared. To this solution was then added a solvent which formed an azeotrope with water, the azeotrope having a boiling point below that of the solvent alone. In addition, the solvent had to be immiscible with water and non-reactive with epichlorohydrin. The azeotrope of the solvent and the water was then distilled off leaving a dispersion of the trialkylammonium chloride in the organic solvent. Thereafter, the trialkylammonium chloride was reacted in the solvent with epichlorohydrin. Such a method was not generally desirable because of the great amount of energy required to distill the water-solvent azeotrope. In addition, existing facilities for manufacturing 3-chloro-2-hydroxypropyl trimethylammonium chloride were not easily retrofitted to employ the process.

SUMMARY OF THE INVENTION

Broadly, the invention is a method of purifying 3-chloro-2-hydroxypropyl trialkylammonium chloride. According to the method of the present invention, there is first prepared an aqueous slurry of 3-chloro-2-hydroxypropyl trialkylammonium chloride which contains impurities typically formed during the reaction of epichlorohydrin with trialkylammonium hydrochloride in an aqueous medium. The slurry has a total solids content from about 70 to about 98 percent by weight of the slurry. Then, a water-miscible alcohol having about 3-4 carbon atoms is mixed with the slurry to form a water-alcohol slurry. Subsequently, precipitated solids are collected from the water-alcohol slurry. The precipitated solids obtained by the method contain a high purity product 3-chloro-2-hydroxypropyl trialkylammonium chloride which can have a purity in excess of 99 percent by weight.

The success of the present method in solving the problem of purifying 3-chloro-2-hydroxypropyl trialkylammonium chloride lies in the surprising discovery that the impurities such as 1,3-bis(trialkylammonium chloride)-2-hydroxypropane, and 1,2-hydroxypropane-3-trialkylammonium chloride remain substantially soluble in the water-alcohol mixture, whereas the desired product, 3-chloro-2-hydroxypropyl trialkylammonium chloride, has limited solubility therein. Thus, the traditional method of producing 3-chloro-2-hydroxypropyl trialkylammonium chloride by reacting epichlorohydrin with trialkylammonium hydrochloride in an aqueous medium can be employed to produce a slurry from which can be obtained substantially pure 3-chloro-2-hydroxypropyl trialkylammonium chloride suitable for use in the manufacture of cationically active starch.

DESCRIPTION OF THE PREFERRED EMBODIMENTS

According to the method of the present invention, there is first prepared an aqueous slurry having a total solids content of from about 70 to about 98 percent by weight of the slurry. In addition to the 3-chloro-2-hydroxypropyl trialkylammonium chloride, which for purposes of convenience is sometimes referred to herein as "the desired product", the slurry may contain substantial quantities of impurities which are typically formed during the reaction of epichlorohydrin with trialkylammonium hydrochloride in an aqueous medium. Thus, conventional methods and equipment known to those in the art can be used to prepare the 3-chloro-2-hydroxypropyl trialkylammonium chloride. The method is not, however, limited to purifying 3-chloro-2-hydroxypropyl trialkylammonium chloride prepared in an aqueous medium, and is useful in purifying the compound prepared in other media as well.

When the impure 3-chloro-2-hydroxypropyl trialkylammonium chloride is obtained as a solid, the aqueous slurry is prepared by simply mixing the powdered or finely divided solid with an appropriate amount of water. When the 3-chloro-2-hydroxypropyl trialkylammonium chloride is prepared by reacting epichlorohydrin with trialkylammonium hydrochloride in an aqueous medium, an aqueous solution containing up to about 70 percent solids by weight of the slurry is typically obtained. Water can be removed from this solution by evaporation or distillation to obtain a slurry with a total solids content of from about 70 to about 98 percent by weight of the slurry. As used herein, the term "total solids content" in reference to a slurry is used to indicate dissolved as well as precipitated solids. Regardless of its method of preparation, the total solids content of the slurry is preferably from about 90 to about 95 percent by weight of the slurry.

Preferably, the water is removed from the aqueous medium reaction product by vacuum distillation at a temperature less than about 50° C. Although the distillation may be performed at a higher temperature, this will not normally be desirable because of the decomposition of the 3-chloro-2-hydroxypropyl trialkylammonium chloride into undesirable by-products.

With the slurry is then mixed a water-miscible alcohol having about 3-4 carbon atoms to form a water-alcohol slurry. The particular alcohol used is not believed to be particularly critical as long as it is miscible with the water. Further, the alcohol mixed with the aqueous slurry does not need to be exceptionally pure and may contain substantial quantities of water and other impurities which are soluble in the resulting water-alcohol slurry. Preferably, however, the amount of such impurities present in the alcohol before mixing with the aqueous slurry is as small as possible. Specific representative examples of such alcohols include isopropanol, n-propanol, t-butanol and the like, with isopropanol being preferred. In comparison with water alone, the 3-chloro-2-hydroxypropyl trimethylammonium chloride is less soluble, yet the impurities typically present remain substantially soluble in the water-alcohol mixture.

The amount of alcohol which may be mixed with the aqueous slurry to exploit the preferential solubility of the impurities over that of the 3-chloro-2-hydroxypropyl trimethylammonium chloride in the resulting alcohol-water mixture ranges from about 10 to about 70 weight percent alcohol, based on the total weight of the resulting alcohol-water slurry, preferably from about 25 to about 50 weight percent the alcohol.

The precipitated solids are then recovered by filtration, or by other means suitable for removing solids from liquid in which the solute is removed with the liquid. The solids so recovered are substantially more pure in the desired product, 3-chloro-2-hydroxypropyl trialklyammonium chloride, than the impure material in the aqueous slurry. The solid filtrate obtained may be used without additional processing, but if desired, may optionally be washed with additional volumes of the alcohol or another non-solvent to remove additional impurities and/or dried to substantially remove any residual alcohol and water.

The liquid water-alcohol filtrate may optionally be disposed of in one or more of several manners. Although it has a higher content of dissolved impurities relative to the desired product than the aqueous slurry, the liquid filtrate may be used as a low grade product, with or without removing the alcohol therefrom by azeotropic distillation or the like. On a continuous commercial scale, however, it is contemplated that a portion of the liquid water-alcohol filtrate is recycled by adding it to the aqueous slurry with make-up alcohol, and disposing of the remaining portion to avoid an excessive accumulation of water and other impurities in the system. Alternatively, the alcohol in the liquid filtrate is recovered by azeotropic distillation. Further, if the alcohol is used to wash the solid filtrate, the alcohol recovered from this step can also be used as make-up alcohol added to the aqueous slurry.

The method is illustrated by way of the following example:

EXAMPLE

An aqueous solution containing about 61 wt. % solids was prepared by reacting epichlorohydrin with trimethylamine hydrochloride in water. The solids had the following analysis:

| Compound | Wt. % of Total Solids | $\sigma_{rel}(\%)^1$ | Analysis Method |
|---|---|---|---|
| 3-chloro-2-hydroxypropyl trimethylammonium chloride | 84.0 | 0.5 | Titration |
| 1,3-Bis(trimethylammonium chloride)-2-hydroxypropane | 9.0 | 8.0 | HPLC |
| 1,2-Hydroxypropane-3-trimethylammonium chloride | 7.0 | 5.0 | HPLC |
| 1,-3-Dichloropropane | 0.0026 | 5.0 | GC |
| Epichlorohydrin | <0.0001 | — | GC |
| Trimethylamine hydrochloride | 0.02 | 5.0 | Titration |

[1] Relative standard deviation.

The solution was reduced to a slurry having about 90 wt. % solids by vacuum distillation at 45° C. To this slurry was added isopropanol in an amount sufficient to obtain 27 wt. % isopropanol in the resulting alcohol-water slurry. The precipitated solids were then collected from the isopropanol-water slurry on a coarse glass frit and washed with two isopropanol aliquots, each of about the same amount used to obtain the alcohol-water slurry. The recovered solids were dried by first passing nitrogen gas through the filter cake, and then overnight in a vacuum oven at 50° C. The product had the following analysis:

| Compound | Wt. % | $\sigma_{rel}(\%)^2$ | Analysis Method |
|---|---|---|---|
| 3-chloro-2-hydroxypropyl trimethylammonium chloride | 99.0 | 0.5 | Titration |
| 1,3-Bis(trimethylammonium chloride)-2-hydroxypropane | <0.5 | | HPLC |
| 1,2-hydroxypropane-3-trimethylammonium chloride | <0.25 | | HPLC |
| 1,3-Dichloropropanol | ≤0.0001 | | GC |
| Epichlorohydrin | <0.0001 | | GC |
| Trimethylamine hydrochloride | <0.01 | | Titration |

[2] See note 1.

As illustrated by the foregoing example, a product of only 84% purity is readily purified according to the method of the invention to have a purity in excess of 99%.

The foregoing disclosure and description of the invention are illustrative and explanatory thereof and various changes in the details may be made without departing from the spirit of the invention.

I claim:

1. A method of purifying 3-chloro-2-hydroxypropyl trialkylammonium chloride, comprising the steps of:
   (a) preparing an aqueous slurry of 3-chloro-2-hydroxypropyl trialkylammonium chloride containing impurities, said slurry having a total solids content of from about 70 to about 98 percent by weight of said slurry;
   (b) mixing therewith a water-miscible alcohol having about 3-4 carbon atoms to form a water-alcohol slurry; and
   (c) collecting precipitated solids from said water-alcohol slurry.

2. The method of claim 1, wherein said solids content of said aqueous slurry is from about 90 to about 95 percent by weight of said slurry.

3. The method of claim 1, wherein said alcohol is present in said water-alcohol slurry in an amount of from about 10 to about 70 percent by weight of said water-alcohol slurry.

4. The method of claim 1, wherein said preparation of said aqueous slurry comprises:
   (i) preparing an aqueous solution of 3-chloro-2-hydroxypropyl trialkylammonium chloride containing impurities formed during the reaction of epichlorohydrin with trialkylammonium hydrochloride; and
   (ii) removing water from said solution to produce an aqueous slurry containing from about 70 to about 98 percent total solids by weight of said aqueous slurry.

5. The method of claim 4, wherein said removal of said water is by vacuum distillation at a temperature less than about 50° C.

6. A method of purifying 3-chloro-2-hydroxypropyl trialkylammonium chloride, comprising the steps of:
   (a) preparing an aqueous solution of 3-chloro-2-hydroxypropyl trialkylammonium chloride containing impurities formed during the reaction of epichlorohydrin with trialkylammonium hydrochloride;
   (b) removing water from said solution by vacuum distillation at a temperature less than about 50° C. to form an aqueous slurry having a total solids content of from about 70 to about 98 percent by weight of said slurry;
   (c) mixing with said slurry a water-miscible alcohol having about 3-4 carbon atoms to form a water-alcohol slurry containing from about 10 to about 70 percent of said alcohol by weight of said water-alcohol slurry; and
   (d) collecting precipitated solids from said water-alcohol slurry.

7. The method of claim 6, wherein said 3-chloro-2-hydroxyproply trialkylammonium chloride is 3-chloro-2-hydroxypropyl trimethylammonium chloride prepared by the reaction of epichlorohydrin with trimethylammonium hydrochloride.

8. The method of claim 7, wherein said reaction of epichlorohydrin with trimethylammonium hydrochloride is in an aqueous medium.

9. The method of claim 6, wherein said aqueous slurry has a total solids content of from about 90 to about 95 percent by weight of said slurry.

10. The method of claim 6, wherein said alcohol is isopropanol.

11. The method of claim 6, wherein said water-alcohol slurry contains from about 25 to about 50 percent of said alcohol by weight of said water-alcohol slurry.

12. The method of claim 6, wherein said precipitated solids are collected by filtration.

13. The method of claim 6, further comprising the step of:
   (e) washing said collected solids with an additional amount of said alcohol.

14. A method of preparing purified 3-chloro-2-hydroxypropyl trimethylammonium chloride, comprising the steps of:
   (a) reacting epichlorohydrin with trimethylamine hydrochloride in an aqueous medium to form an aqueous solution of 3-chloro-2-hydroxypropyl trimethylammonium chloride containing impurities;
   (b) removing water from said solution by vacuum distillation at a temperature less than about 50° C. to form an aqueous slurry having a total solids content of from about 90 to about 95 percent by weight of said slurry;
   (c) mixing with said slurry a water-miscible alcohol having about 3-4 carbon atoms to form a water-alcohol slurry containing from about 25 to about 50 percent of said alcohol by weight of said water-alcohol slurry;
   (d) filtering said water-alcohol slurry to collect precipitated solids; and
   (e) washing said collected solids with an additional amount of said alcohol.

15. The method of claim 14, wherein said alcohol is isopropanol.

16. The method of claim 14, wherein at least a portion of said alcohol mixed with said slurry in step (c) comprises said alcohol recovered from washing said solids in step (e).

17. The method of claim 14, further comprising the steps of:
   (f) collecting liquid filtrate from step (d); and
   (g) recycling a portion of said filtrate by mixing said portion with said slurry in step (c), said filtrate replacing at least some of said alcohol in said step.

18. The method of claim 17, wherein said recycled portion of said liquid filtrate is azeotropic distillate of said liquid filtrate.

* * * * *